United States Patent
Saravanamurugan et al.

(10) Patent No.: US 10,189,768 B2
(45) Date of Patent: Jan. 29, 2019

(54) PROCESS FOR HYDROGENOLYSIS OF ALPHA-HYDROXY ESTERS OR ACIDS USING A HETEROGENEOUS CATALYST

(71) Applicant: DANMARKS TEKNISKE UNIVERSITET, Lyngby (DK)

(72) Inventors: Shunmugavel Saravanamurugan, Punjab (IN); Santosh Govind Khokarale, Umeå (SE); Anders Riisager, Taastrup (DK)

(73) Assignee: Danmarks Tekniske Universitet, Lyngby (DK)

( * ) Notice: Subject to any disclaimer, the term of this patent is extended or adjusted under 35 U.S.C. 154(b) by 0 days.

(21) Appl. No.: 15/739,378

(22) PCT Filed: Jun. 23, 2016

(86) PCT No.: PCT/EP2016/064573
§ 371 (c)(1),
(2) Date: Dec. 22, 2017

(87) PCT Pub. No.: WO2017/001285
PCT Pub. Date: Jan. 5, 2017

(65) Prior Publication Data
US 2018/0170853 A1 Jun. 21, 2018

(30) Foreign Application Priority Data
Jun. 25, 2015 (EP) .................... 15173952

(51) Int. Cl.
*C07C 67/327* (2006.01)
*C07C 69/24* (2006.01)
(52) U.S. Cl.
CPC .................. *C07C 67/327* (2013.01)
(58) Field of Classification Search
CPC ................. C07C 69/24; C07C 67/327
See application file for complete search history.

(56) References Cited

U.S. PATENT DOCUMENTS 4,792,620 A * 12/1988 Paulik .................. B01J 31/0231
560/232

FOREIGN PATENT DOCUMENTS

| EP | 0031606 | 7/1981 |
| EP | 0036939 | 10/1981 |
| WO | WO 2015/030580 A1 | 3/2015 |

OTHER PUBLICATIONS

Norskov et al, Nature Chemistry, Towards the Computational Design of Solid Catalysts, 2009, 1, pp. 37-46. (Year: 2009).*
Serrano-Ruiz et al, Green Chemistry, Catalytic Upgrading of Lactic Acid to Fuels and Chemicals by Dehydration/hydrogenation and C—C Coupling Reactions, 2009, 11, pp. 1101-1104. (Year: 2009).*
Fan et al, Chemistry Letters, Efficient Hydrogenation of Ethyl Lactate to 1,2-Propanediol over Ru-B/TiO2 in Aqueous Solution, 2008, 7(8), pp. 852-853. (Year: 2008).*
Eastham et al., "Synthesis and spectroscopic characterization of all the intermediates in the Pd-catalysed methoxycarbonylation of ethane", Chem. Commun., 2000, 609-610.
van Beek et al., "Synthesis of methyl propanoate by Baeyer-Villiger monooxygenasees", Chem. Commun., 2014, 50, 13034-13036.
Xue et al., "Effect of Metal Additives on Structure and properties of a Co/SiO$_2$ Hydrogenation Catalyst", Chinese Journal of Catalysis, 2012, 33, 1642-1649.

\* cited by examiner

*Primary Examiner* — Paul A Zucker
(74) *Attorney, Agent, or Firm* — Baker & Hostetler LLP

(57) ABSTRACT

The present invention relates to a method for hydrogenolysis of alpha-hydroxy esters or acids, comprising reacting the alpha-hydroxy ester or acid in the presence of a heterogeneous catalyst. The present invention also relates to a method for producing propionic acid ester, and the use of any of the methods for the production of propionic acid esters, such as alkyl propionate.

19 Claims, 5 Drawing Sheets

PROCESS FOR HYDROGENOLYSIS OF ALPHA-HYDROXY ESTERS OR ACIDS USING A HETEROGENEOUS CATALYST

CROSS-REFERENCE TO RELATED APPLICATIONS

This application is the National Stage of International Patent Application No. PCT/EP2016/064573 filed Jun. 23, 2016, which clls the benefit of European application number 15173952.1, filed Jun. 25, 2015, the disclosures of which are incorporated herein by reference in their entireties.

FIELD OF INVENTION

The present invention relates to a method for hydrogenolysis of alpha-hydroxy esters or acids, and to a method for producing propionic acid esters. The present invention further relates to the use of any of the methods for the production of propionic acid esters, such as alkyl propionate.

BACKGROUND OF INVENTION

Substitutes for fossil fuels are of importance due to the diminishing fossil fuel reserves and increasing atmospheric $CO_2$ levels. Biomass is a promising substitute in many applications where fossil fuels have traditionally been used. Biomass may be converted into transportation fuels, as well as used in the chemical industry for the production of fine chemicals, such as acrylic plastics. Furthermore, biomass is both a renewable and $CO_2$-neutral source.

However, in contrast to conventional fossil fuels such as petroleum based feedstock, biomass is a lignocellulosic feedstock which has a high oxygen to carbon mole ratio due to oxygenated groups such as —OH, —OR (where R denotes a carbon chain), —C=O, and —COOH. The oxygen/carbon ratio results in uncontrolled decomposition with temperature, as well as low volatility, high reactivity, and high solubility in water.

Thus, in contrast to the conventional fossil feedstock, biomass cannot be used directly in the main streams for fuel or for the chemical industry. Biomass derived molecules therefore needs to be further processed to reduce the oxygen content. A known route to de-functionalise molecules is hydrogenolysis.

The biomass derived molecules include alpha-hydroxy acids and esters (also written as α-hydroxy) such as lactic acid and alkyl esters of lactic acid, e.g. alkyl lactates, such as methyl lactate. In an alpha-hydroxy acid or esters, the hydroxyl group is attached to the carbon atom carrying the carboxyl or carbonyl group. The hydrogenolysis of the alpha-hydroxy esters as lactic acid or alkyl lactates may result in alkyl propionate, such as methyl propionate. Methyl propionate is also known as an important chemical precursor in the production of acrylic plastics. The hydrogenolysis of methyl lactate to methyl propionate is illustrated in reaction (R-I).

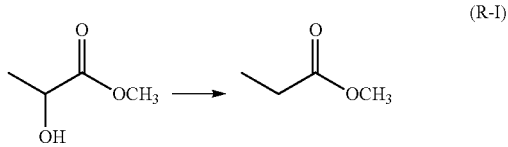

(R-I)

Methyl propionate is traditionally not produced based on biomass and hydrogenolysis. Instead it has been based on fossil feedstock molecules, such as the methoxycarbonylation of ethylene with carbon monoxide (CO), methanol, and a homogeneous palladium (Pd)—phosphine complex as catalyst [1]. However, the traditional production process suffers from drawbacks such as the requirement for poisonous gas (CO), the expensive catalyst materials, and in many cases, the dependence on fossil feedstock molecules.

Thus, the synthesis of methyl propionate by alternative methods such as hydrogenolysis of biomass derived molecules is receiving increasing interest. Xiu et al. [2] described the hydrogenolysis of ethyl lactate, resulting in several different products including ethyl propionate. The hydrogenolysis is catalysed by a heterogeneous; cobalt (Co) based bimetallic catalyst made of Co-M, where M can be Zn, Fe, Cu, or Sn, and where the catalyst is supported by $SiO_2$. The addition of Fe was disclosed to increase the selectivity to ethyl propionate, however the catalysts did not provide a high conversion or a high yield of the propionate.

Furthermore, heterogeneous catalysts of noble metals (such as Ru, Re), and other metals such as Ni, Cu, Fe, and Co have further been shown to catalyse hydrogenolysis processes, e.g. the hydrogenolysis of polyols. However, an efficient catalytic process for the hydrogenolysis of alpha-hydroxy esters (such as alkyl lactate) to alkyl propionate has not been disclosed.

The production of methyl propionate by other alternative methods, such as enzymatic catalysis has also been described [3]. However, the methods were not efficient and showed low selectivity of methyl propionate.

References

[1] G. R. Eastham, B. T. Heaton, J. A. Iggo, R. P. Tooze, R. Whyman, S. Zacchini, *Chem. Commun*, 2000, 609

[2] J. Xiu et al., *Chin. J. Catal.*, 2012, 33, 1642.

[3] H. L. van Beek, R. T. Winter, G. R. Eastham, M. W. Fraaije, *Chem. Commun.*, 2014, 50, 13034.

SUMMARY OF INVENTION

Considering the prior art described above, it is an object of the present invention to provide an alternative method for the hydrogenolysis of alkyl lactates and the production of alkyl propionates. The alternative method further provides a cheaper catalytic system for producing propionic acid esters, such as alkyl propionate, as well as a more efficient route for the synthesis with surprisingly high conversion and yield.

The first aspect of the invention relates to a method for hydrogenolysis of alpha-hydroxy esters or acids, comprising:

reacting the alpha-hydroxy ester or acid in the presence of a solid catalyst and a catalyst support, wherein the catalyst comprises at least one metal selected from the group of metals belonging to groups 6-12 and periods 4-6 of the periodic table, and wherein the catalyst support is a porous solid material with the proviso that the porous solid material is not consisting of $SiO_2$.

The second aspect of the invention relates to a method for producing a propionic acid ester with the formula:

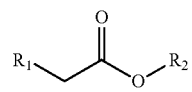

wherein $R_1$ is methyl, and $R_2$ is selected from the group of: hydrogen, alkyl, halogenated alkyl, aminoalkyl, hydroxyalkyl, alkoxyalkyl, alkenyl, alkynyl, aryl, heteroaryl, cycloalkyl, cycloalkenyl, heterocycloalkyl, and heterocycloalkenyl, comprising the steps of:
(i) providing an alpha-hydroxy ester,
(ii) providing a solid catalyst and a catalyst support,
   wherein the catalyst comprises at least one metal selected from the group of metals belonging to groups 6-12 and periods 4-6 of the periodic table, and
   wherein the catalyst support is a solid material with the proviso that the solid material cannot consist of $SiO_2$, and
(iii) reacting the alpha-hydroxy ester in the presence of the catalyst and catalyst support,
whereby the alpha-hydroxy ester is converted into propionic acid ester.

A further aspect of the invention relates to any use of the methods according either the first aspect or the second aspect of the invention, for the production of propionic acid esters, such as alkyl propionate, more preferably methyl propionate, ethyl propionate, and butyl propionate.

DESCRIPTION OF DRAWINGS

The invention will in the following be described in greater detail with reference to the accompanying drawings.

Reaction conditions: 2.0 mmol MeL, 100 mg catalyst (Fe—Ni/$ZrO_2$, Fe=0.05 mmol or 2.68 wt. %, Ni=0.025 mmol or 1.40 wt. %), 8 g MeOH, 220° C. reaction temperature, 12 hours reaction time, total pressure 50 bar with addition of $N_2$ gas if required, 40 mg naphthalene (internal standard). Catalyst activated at 450° C. in air followed by reduction at 300° C. for 3 hours under formier gas flow (10 vol. % $H_2$ in $N_2$, 50 ml/min), except for the non-reduced catalyst, where the reduction step is not carried out.

Figure 5:
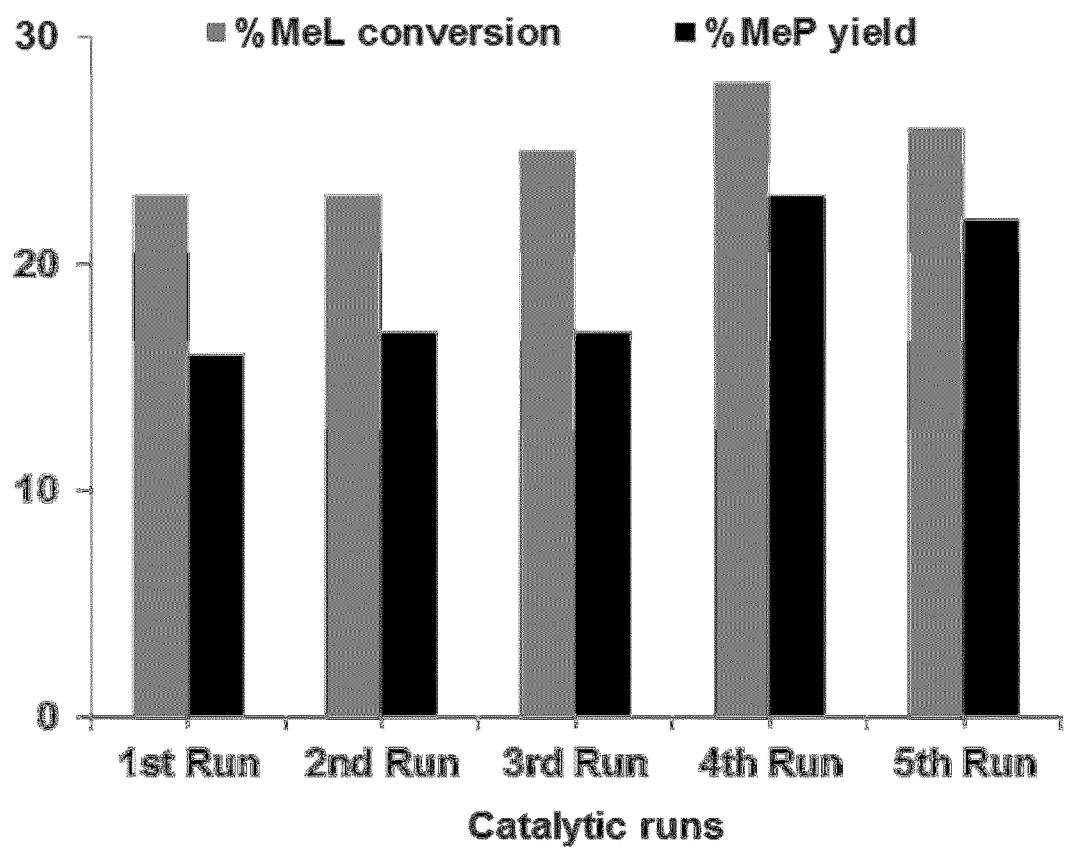

FIG. 5 shows the results of Example 9, and illustrates the catalytic activity in the methyl lactate (MeL) hydrogenolysis process as the conversion of MeL and the yield of MeP, for a Fe—Ni/$ZrO_2$ catalyst that is recycled for up to 5 consecutive catalytic runs. Reaction conditions: 100 mg catalyst (Fe=0.05 mmol or 2.68 wt % and Ni=0.01 mmol or 0.58 wt %), 8 g MeOH, 3 hours reaction time, 220° C. reaction temperature, 52 bar $H_2$ gas pressure, 40 mg naphthalene (internal standard). Catalyst activated at 450° C. in air followed by reduction at 300° C. for 3 hours under formier gas flow (10 vol. % $H_2$ in $N_2$, 50 ml/min).

DETAILED DESCRIPTION OF THE INVENTION

The conversion of biomass derived molecules with high oxygen/carbon ratio into industrial relevant molecules with lower oxygen/carbon ratio (also called platform molecules) is receiving increasing focus as biomass is replacing fossil fuels in more and more applications. Typical oxygenated biomass derived molecules include alpha-hydroxy esters, lactic acid and alkyl esters of lactic acid, such as alkyl lactates, e.g. methyl lactate (MeL).

The oxygenated molecules can be de-functionalised by a hydrogenolysis reaction, and for the reaction to run efficiently, a catalyst and a catalytic method can be applied.

Thus, a promising route to successfully replace fossil with biomass derived molecules, is a cost-effective and efficient catalytic method for the hydrogenolysis of alpha-hydroxy esters, such as lactic acids and alkyl lactates.

The industrial relevant molecules (platform molecules) which the biomass derived molecules may be converted into, include alkyl propionates, such as methyl propionate (MeP). The alkyl propionates may be used as platform molecules for different applications, e.g as for precursors in the production of fine chemicals. As an example, methyl propionate is known to be a key precursor in the production of acrylics, such as methyl methacrylate (MMA) and poly (methyl methacrylate) (PMMA).

The present invention provides a novel method for the hydrogenolysis of alpha-hydroxy esters, such as alkyl lactates, and the production of alkyl propionates. The novel methods provide alternative and cheaper methods for the hydrogenolysis of the alpha-hydroxy ester, such as alkyl lactates, and the production of alkyl propionate. The novel methods also provide a surprisingly efficient route for the hydrogenolysis and the production of alkyl propionates, with the methods showing surprisingly high conversions of the alpha-hydroxy esters, such as alkyl lactate, and surprisingly high yields of the alkyl propionate.

The novel methods are based on a heterogeneous catalytic system, comprising a solid catalyst and a porous solid catalyst support. It is known to a person skilled in the art that the activity, or performance, of a catalytic system is to a high degree determined by the material properties, such as the elements present in the catalyst and the material of the support. The catalytic active sites and the catalytic activity also depend on the crystallographic orientation and dispersion of the catalyst, which may be a function of the catalyst-support interactions. Other parameters influencing on the catalyst activity include reaction parameters such as temperature, pressure, time, reactant types (substrates) and reactant concentrations.

The catalytic activity, or performance, may be indicated by conversion, yield, and/or selectivity. The conversion indicates the number of converted feedstock molecules relative to the total feedstock. The feedstock molecules may also be referred to as substrate or reactants, such as the methyl lactate shown in reaction (R-I).

The yield refers to the number of feedstock molecules (reactants) converted into the desired product, relative to the total feedstock. The desired product could be methyl propionate as shown in reaction (R-I). The selectivity refers to the number of the desired product molecules, relative to the number of converted reactants.

For the current invention, various heterogeneous catalytic systems were tested for the hydrogenolysis of methyl lactate (MeL) into methyl propionate (MeP). The tests including different types of catalyst material and catalyst support materials are summarised in Examples 1-5 and 11.

In Example 1, various catalysts of precious metals and precious bimetallic compositions were tested on different supports. The tests further included different pre-treatment of the catalyst, and different reaction temperature. The tests are further described in Example 1, and the results are summarised in Table 1. From Table 1 it was seen that different catalytic performance for the MeL to MeP reaction was obtained with different support materials, and good catalytic performance was especially observed with metal oxide supports, except for the support consisting of only $SiO_2$.

In Example 2, zirconia ($ZrO_2$) supported catalysts with various catalyst of bimetallic compositions, were tested. The results are summarised in Table 2, and further described in Example 2. From Table 2 it was seen that good catalytic performance for the MeL to MeP reaction could also be obtained using less precious metals, such as bimetallic composition including non-precious metals.

In Example 3, catalytic systems comprising only non-precious metals were tested. The results are summarised in Table 3, and further described in Example 3. Surprisingly high catalytic performance for the MeL to MeP reaction was observed using these metals.

In general, Table 1-3 showed that good catalytic activity was observed with metals, and bimetallic compositions with metals, belonging to groups 6-12 and periods 4-6 of the periodic table.

In Example 4, the supported Fe—Ni catalysts were tested on different support materials. The results are summarised in Table 4, and further described in Example 4. In accordance with the results with precious metals (cf. Example 1), better performance was observed with metal oxide supports, except for the support consisting of only $SiO_2$.

In Example 5, the Fe—Ni catalysts on a $ZrO_2$ support (also abbreviated as Fe—Ni/$ZrO_2$ catalysts) with different Fe/Ni molar ratios, were tested. The results are summarised in FIG. 1, and further described in Example 5. In general, a slightly better activity was observed with increasing Ni content.

In Example 11, catalysts of nickel ferrite ($NiFe_2O_4$) and cobalt ferrite ($CoFe_2O_4$) were tested. The results are summarised in Table 7, and further described in Example 11. High catalytic performances for the MeL to MeP reaction were observed for both the nickel ferrite and cobalt ferrite, with conversion degrees above 99% and yields of respectively 75% and 71%.

Based on tested catalytic systems, it was seen that surprisingly high catalytic performance for the MeL to MeP conversion could be obtained with the described heterogeneous catalytic systems, comprising metals, and bimetallic compositions with metals, belonging to groups 6-12 and periods 4-6 of the periodic table, in combination with a catalyst support that is not $SiO_2$.

Thus, in an embodiment of the invention, a method is provided for hydrogenolysis of alpha-hydroxy esters or acids, comprising: reacting the alpha-hydroxy ester or acid in the presence of a solid catalyst and a catalyst support, wherein the catalyst comprises at least one metal selected from the group of metals belonging to groups 6-12 and periods 4-6 of the periodic table, and wherein the catalyst support is a porous solid material with the proviso that the solid material is not consisting of $SiO_2$.

What is presented herein is a catalyst system or a solid catalyst composed of a support with active metals. Thus, the support may also be active in the catalytic process.

The tested catalytic metals selected from the group of metals belonging to groups 6-12 and periods 4-6 of the periodic table have different properties, including variations in the catalytic activity, different raw material costs, and may have other properties, such as radioactivity as e.g. technetium (Tc). However, radioactive materials are not advantageous for a product or a method, due to health and environment concerns.

In a further embodiment of the invention, the catalyst comprises at least one metal selected from the group of: Cr, Mn, Fe, Co, Ni, Cu, Zn, Mo, Ru, Rh, Pd, Ag, Cd, W, Re, Os, Ir, Pt, Au, Hg, and combinations thereof, more preferably selected from the group of: Mn, Fe, Co, Ni, Cu, Zn, Re, Pt, Au, and combinations thereof, and most preferably selected from the group of: Mn, Fe, Co, Ni, Cu, Zn, and combinations thereof.

In a further embodiment of the invention, the catalyst is a ferrite or a combination of one or more ferrites, such as nickel ferrite ($NiFe_2O_4$) and/cobalt ferrite ($CoFe_2O_4$).

Surprisingly high catalytic activity was observed for bimetallic compounds comprising iron (cf. Tables 2-4 and FIG. 5). In a further embodiment of the invention, the catalyst is a bimetallic compound comprising iron (Fe), more preferably selected from the group of: Fe—Re, Fe—Mo, Fe—Mn, Fe—Cu, Fe—Co, and Fe—Ni, most preferably selected from the group of: Fe—Co, and Fe—Ni.

High catalytic activity was also observed for bimetallic compounds comprising rhenium (Re). In another embodiment of the invention, the catalyst is a bimetallic compound comprising rhenium (Re), more preferably selected from the group of: Ru—Re, Rh—Re, Ag—Re, Au—Re, Ir—Re, Pd—Re, Pt—Re, Fe—Re, most preferably selected from the group of: Ru—Re, Ag—Re, Au—Re and Fe—Re.

The catalyst system comprises both the catalyst material and the catalyst support, and the support influences on the interactions in the system, as well as the catalyst activity. The tested catalytic systems included different types of catalyst support, where the catalyst support was a porous solid material.

In an embodiment of the invention, the catalyst support comprises one or more metal oxide(s), and/or a thermally stable polymer, and/or activated carbon, with the proviso that if the support consists of one metal oxide, said metal oxide is not $SiO_2$.

Surprisingly high catalytic activity was observed with catalyst supports of metal oxides, except for supports consisting of only $SiO_2$. In a further embodiment of the invention, the catalyst support is a metal oxide, with the proviso that said metal oxide is not $SiO_2$. In a further embodiment of the invention, the metal oxide is selected from the group of: $ZrO_2$, $TiO_2$, $Al_2O_3$, $MgAl_2O_4$, zeolites, or zeotype material with aluminium or silicium partially substituted with other metals, combinations thereof, and any combination with $SiO_2$, more preferably selected from the group of: $ZrO_2$ and $TiO_2$, and most preferably is $ZrO_2$.

In another embodiment of the invention, the catalyst support is a thermally stable polymer selected from the group of: polyether (ether) ketone (PEEK), polyethersulfone (PES), polyphenylquinoxaline (PPQ), polybenzimidazole (PBI), polyimide (PI), poly(arylene ether), poly(imino ether), polyaniline, polyphenylene, polydivinylbenzene (PDVB), polyacrylates (PA), and poly-methylmethacrylates (PMMA).

It is known to the skilled person within the art that a heterogeneous catalyst support material preferably should be a porous solid. The catalyst support may be of any porosity, such as macroporous, where the pores and pore size distribution is above 50 nm, and/or mesoporous, where the pores and pore size distribution is in the range of 2-50 nm, and/or microporous, where the pores and pore size distribution is below 2 nm. In an embodiment of the invention, the catalyst support is microporous and/or mesoporous. In a further embodiment of the invention, the catalyst support is a microporous material, such as a zeolite.

The catalytic systems of Examples 1-5 were investigated for the reaction of converting MeL to MeP. The skilled person in the art would know that the catalytic performance may be similar for any alpha-hydroxy esters, i.e. reactants similar to MeL.

In Example 10, the influences of different substrates, i.e. different types of alpha-hydroxy esters, were tested for the Fe—Ni/$ZrO_2$ catalyst. The results are further described in Example 10, and summarised in Table 6. As seen in Table 6, the catalytic system was found to be active and selective with more than 99% alkyl lactate conversions, as well as >65% selectivities for all the substrates and corresponding alkyl propionates.

In an embodiment of the invention, the alpha-hydroxy ester has the formula:

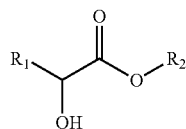

wherein $R_1$ and $R_2$ are independently selected from the group of: hydrogen, alkyl, halogenated alkyl, aminoalkyl, hydroxyalkyl, alkoxyalkyl, alkenyl, alkynyl, aryl, heteroaryl, cycloalkyl, cycloalkenyl, heterocycloalkyl, and heterocycloalkenyl.

In a further embodiment of the invention, the alpha-hydroxy ester is an alkyl lactate. In yet a further embodiment of the invention the alkyl lactate is methyl lactate.

In a further embodiment of the invention, $R_1$ and $R_2$ are independently selected from $C_1$-$C_9$ alkyl and hydrogen, more preferably $C_1$-$C_3$ alkyl and hydrogen, and most preferably $R_1$ is methyl and $R_2$ is methyl or hydrogen.

Other parameters than the materials of the catalytic system is known to influence on the catalyst activity for a reaction, e.g. reaction parameters such as temperature, pressure, time, reactant types (substrates) and reactant concentrations. For the current invention, the Fe—Ni/$ZrO_2$ catalytic systems were tested for the hydrogenolysis of methyl lactate (MeL) into methyl propionate (MeP) under different reaction conditions, and the results are summarised in FIGS. 2-4, and Examples 6-8.

In Example 6, the influence of the reaction temperature for the Fe—Ni/$ZrO_2$ catalyst is tested. The results are summarised in FIG. 2. Better catalytic performance for the MeL conversion to MeP, or the production of MeP, was seen around 220° C. In an embodiment of the invention, the method is carried out in the temperature range between 150-300° C., more preferably between 200-280° C., and most preferably between 220-240° C.

In Example 6, the influence of the reaction time for the Fe—Ni/$ZrO_2$ catalyst is tested. The results are summarised in FIG. 3, where it can be observed that both the conversion and MeP selectivity increased with time. In an embodiment of the invention, the method is carried out with a reaction time between 1-30 hours, more preferably between 10-25 hours, and most preferably between 12-20 hours.

A hydrogen source is needed for the hydrogenolysis reaction to take place to a significant degree. In an embodiment of the invention, the process is carried out at elevated pressure and temperature, and in the presence of a hydrogen source.

In Example 7, the influence of the partial pressure of hydrogen ($H_2$) for the Fe—Ni/$ZrO_2$ catalysts of the invention were tested. The results are summarised in FIG. 4, and further described in Example 8. The hydrogen may be introduced directly as molecular $H_2$ gas, and from FIG. 4 it is seen that increasing the partial pressure of the hydrogen gas resulted in minor increase in the yield and selectivity. However, it is also seen that the expensive pure $H_2$ gas are not necessary and can replaced by the cheaper and more safe to handle formier gas mixture (10 vol % $H_2$ in $N_2$).

Figure 4:
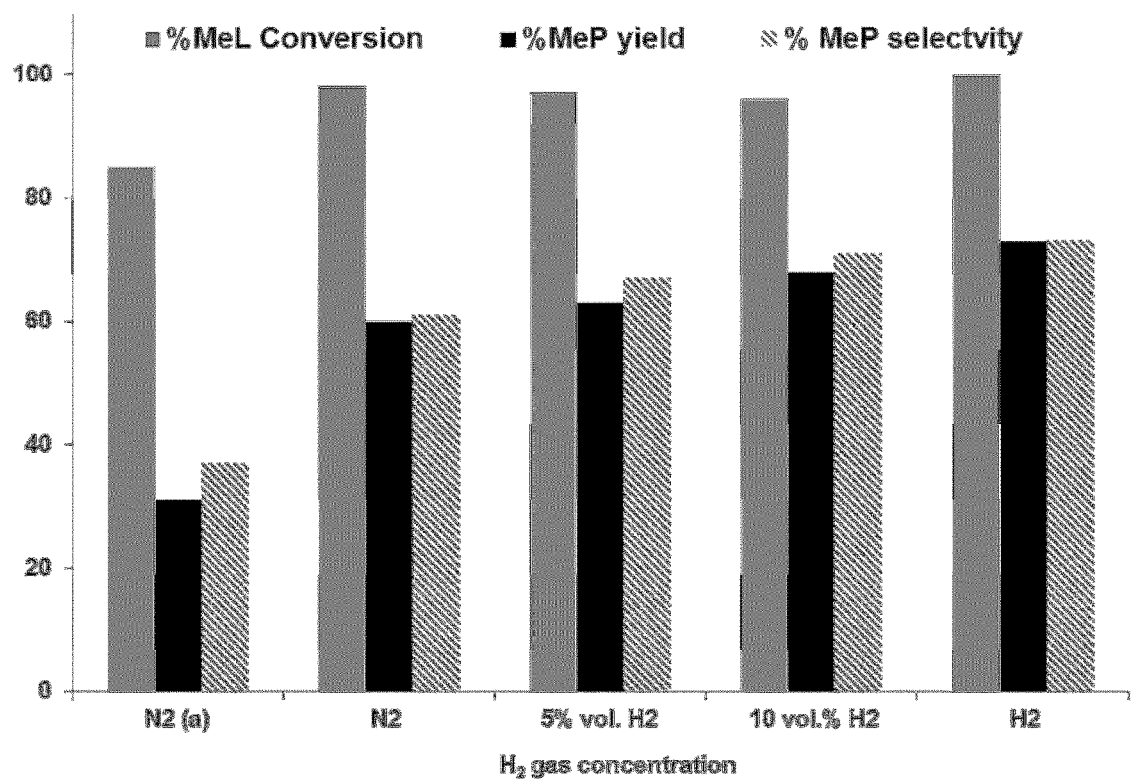
FIG. 4 shows the results of Example 7, and illustrates the catalytic activity in the methyl lactate (MeL) hydrogenolysis process as the converted MeL, the yield of MeP, and the selectivity of MeP, for Fe—Ni/$ZrO_2$ catalysts at different partial pressure of $H_2$ gas, and in $N_2$ gas with a reduced and non-reduced Fe—Ni/$ZrO_2$ catalysts (non-reduced indicated as N2(a)).

Example 7 and FIG. 4 further surprisingly showed the possibility of relatively high catalytic activity of the Fe—Ni catalyst in the absence of directly added molecular $H_2$. The observed catalytic activity in the pure $N_2$ atmosphere can be ascribed to in-situ generation of molecular $H_2$ due to catalytic decomposition (i.e. reforming) of the organic solvent, in this case methanol ($CH_3OH$). The molecular $H_2$, which originated from MeOH, will both assist in the hydrogenolysis process, as well as assist in the reduction of any non-reduced Fe and Ni oxide species, such as in the case with non-reduced catalyst.

In an embodiment of the invention, the hydrogen source is a gas comprising $H_2$ and/or a component, which may be a fluid, decomposing into hydrogen, more preferably the hydrogen source is a gas comprising $H_2$. In a further embodiment of the invention, the hydrogen source is selected from the group of: alcohols, methyl formate, formic acid, diimide, and hydrazine, more preferably selected from the group of: methanol, ethanol, butanol, propanol and isopropanol, and most preferably is methanol.

In Example 8, the influence of the reactant concentration (i.e. MeL concentration) for the Fe—Ni/$ZrO_2$ catalyst is tested. The results are summarised in Table 5, and it was observed that the MeL conversion and MeP yield decreased gradually with the increase in MeL concentration in the reaction mixture. In an embodiment of the invention the MeL concentration is between 1-10 mmol, more preferably between 1 to 5 mmol, and most preferably between 1.5 to 3 mmol.

Another aspect of the invention is directed to a method for producing propionic acid esters, such as alkyl propionate. In an embodiment of the invention, a method is provided for producing propionic acid ester with the formula:

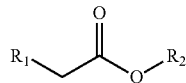

wherein $R_1$ is methyl, and $R_2$ is selected from the group of: hydrogen, alkyl, halogenated alkyl, aminoalkyl, hydroxyalkyl, alkoxyalkyl, alkenyl, alkynyl, aryl, heteroaryl, cycloalkyl, cycloalkenyl, heterocycloalkyl, and heterocycloalkenyl, comprising the steps of:
(i) providing an alpha-hydroxy ester,
(ii) providing a solid catalyst and a catalyst support,
  wherein the catalyst comprises at least one metal selected from the group of metals belonging to groups 6-12 and periods 4-6 of the periodic table, and
  wherein the catalyst support is a solid material with the proviso that the solid material cannot consist of $SiO_2$, and
(iii) reacting the alpha-hydroxy ester in the presence of the catalyst and catalyst support,
whereby the alpha-hydroxy ester is converted into propionic acid ester.

In the preferred embodiment of the invention, R1 is a methyl group. In another embodiment of the invention, the propionic acid ester is selected from the group of: alkyl propionate, aryl propionate, and alkenyl propionate. When the propionic acid ester is an alkyl propionate $R_2$ is selected from the group of: hydrogen, alkyl, halogenated alkyl, aminoalkyl, hydroxyalkyl, alkoxyalkyl, cycloalkyl, and heterocycloalkyl, When the propionic acid ester is aryl propionate $R_2$ is selected from the group of: aryl and heteroaryl, When the propionic acid ester is an alkenyl propionate $R_2$ is selected from the group of: alkenyl, alkynyl, cycloalkenyl, and heterocycloalkenyl, In a further embodiment of the invention, the propionic acid ester is alkyl propionate. In a further embodiment, the propionic acid ester is methyl propionate. Thus in an embodiment $R_1$ and $R_2$ are methyl.

Examples 1-9 also relate to the method of producing alkyl propionate. Thus, the method of hydrogenolysis of alpha-hydroxy esters and the method of producing alkyl propionate are related.

In an embodiment of the method for producing propionic acid ester, such as alkyl propionate, the alpha-hydroxy ester is an alkyl lactate. In a further embodiment of the invention, the alkyl lactate is methyl lactate.

In another embodiment of the invention, the alkyl propionate is methyl propionate.

Similarly to the method of hydrogenolysis reaction, the method of producing propionic acid ester, such as alkyl propionate, according to the aspect of the present invention is advantageously carried out in at elevated temperature and pressure, and in the presence of a hydrogen source. In an embodiment of the invention, step (iii) in the method of producing alkyl propionate, is carried out at elevated pressure and temperature, and in the presence of a hydrogen source. In a further embodiment of the invention, the hydrogen source is a gas comprising $H_2$ and/or a constituent decomposing into hydrogen, more preferably the hydrogen source is a gas comprising $H_2$. In a further embodiment of the invention, the hydrogen source is selected from the group of: alcohols, methyl formate, formic acid, diimide, and hydrazine, more preferably selected from the group of: methanol, ethanol, butanol, propanol and isopropanol, and most preferably is methanol.

To reduce the costs, and simplifying a method of a hydrogenolysis reaction, or the method of producing propionic acid ester, such as alkyl propionate, according to the aspects of the current invention, the reactions may be performed in batches or continuously. In an embodiment of the invention, the method is selected from the group of: a batch process, a continuous process, such as a continuous flow fixed-bed process and/or fluidized-bed flow process.

To further reduce costs and simplify the overall methods, the catalytic systems may be recycled. In Example 9, a Fe—Ni/$ZrO_2$ catalyst was efficiently recycled up to 5 times. The results are also summarised in FIG. 5. In an embodiment of the invention, the catalyst system, comprising the solid catalyst and the catalyst support, is recycled. In a preferred embodiment of the invention, the catalyst system is recycled more than 2 times, and most preferably more than 4 times.

EXAMPLES

Example 1

Different Supported Precious Metal Catalyst

The catalytic activity of Ru, Re, and bimetallic Ru—Re catalysts on different support materials was tested for the hydrogenolysis of methyl lactate (MeL) to methyl propionate (MeP). The support materials included activated carbon (AC), and the oxide supports $TiO_2$, $SiO_2$, and $ZrO_2$.

The results are summarised in Table 1, showing the MeL conversion (Conv.) in %, and the MeP yield in %. [a] Reaction condition: 2.0 mmol MeL, 100 mg catalyst (Ru=0.05 mmol, 0.025 mmol Re), 8 g MeOH, 50 bar $H_2$ gas pressure, 12 hours reaction time, 220° C. reaction temperature, 40 mg naphthalene (internal standard), [b] non-activated catalyst, [c] catalyst activated at 450° C. in Ar. [d] Catalyst activated at 450° C. in air. Reduction at 300° C. for 3 hours under formier gas flow (10 vol. % $H_2$ in $N_2$, 50 ml/min).

TABLE 1

| MeL to MeP conversion with supported Ru and Re metal catalysts[a] | | | |
|---|---|---|---|
| Entry | Catalyst | Temp. ° C. | % MeL Conv. | % MeP yield |
| 1 | Ru/AC[b] | 200 | 12 | 7 |
| 2 | Re/AC[b] | 200 | 8 | 3 |
| 3 | Ru—Re/AC[b] | 200 | 89 | 20 |
| 4 | Ru—Re/AC[b] | 220 | 97 | 24 |
| 5 | Ru—Re/AC[c] | 220 | 63 | 32 |
| 6 | Ru—Re/$TiO_2$[d] | 220 | 61 | 20 |
| 7 | Ru—Re/$SiO_2$[d] | 220 | 49 | 18 |
| 8 | Ru—Re/$ZrO_2$[d] | 220 | 86 | 30 |

The catalysts and support material were synthesised using techniques known to the skilled person in the art. The bimetallic catalysts were made of 0.05 mmol or 5 wt % Ru and 0.025 mmol or 4.71 wt % Re (for 100 mg catalyst).

The catalysts were either (b) not further activated, or (c) activated at 450° C. in argon (Ar), or (d) activated at 450°

C. in air followed by reduction at 300° C. for 3 hours under formier gas flow (10 vol. % $H_2$ in $N_2$, 50 ml/min).

The catalytic reaction was carried out in a batch process with 2.0 mmol MeL (208.12 mg), 100 mg catalyst, 8 g methanol (MeOH), 40 mg naphthalene, and at 50 bar $H_2$ gas pressure, and with 12 hours reaction time, and at 200 or 220° C. reaction temperature.

From Table 1 it is seen that the activated carbon supported metals Ru and Re (respectively, Ru/AC and Re/AC) showed 12% and 8% MeL conversion with 7% and 3% MeP yields (cf. Table 1, entry 1 and 2). The bi-metallic Ru—Re/AC catalyst under identical conditions exhibits 20% MeP yield, showing a synergic effect of the bi-metallic combination (cf. Table 1, entry 3).

Further increase in the reaction temperature to 220° C. showed a small increase in the MeP yield to 24% (cf. Table 1, entry 4), and a further pre-activation of the Ru—Re/AC catalyst at 450° C. prior to reaction enhanced the MeP yield to 32% (cf. Table 1, entry 5).

Table 1, entry 6-8, shows the activity of the bimetallic Ru—Re catalyst supported by the oxide supports $TiO_2$, $SiO_2$ and $ZrO_2$ under identical reaction conditions. It was observed that similar to Ru—Re/AC catalyst, the Ru—Re/$ZrO_2$ catalyst showed equivalent catalytic performance with 30% MeP yield (vs 32% for Ru—Re/AC). The $TiO_2$ and $SiO_2$ catalyst showed relatively lower catalytic activity compared to the $ZrO_2$ supported bimetallic catalysts.

Example 2

$ZrO_2$ Supported M-Re Catalysts

The catalytic performance in the methyl lactate (MeL) hydrogenolysis process was tested for $ZrO_2$ supported, bimetallic M-Re catalysts, where M was Ru, Rh, Ag, Au, Ir, Pd, Pt, or Fe.

The results are summarised in Table 2, showing the MeL conversion (Conv.) in %, and the MeP yield in %. [a] Reaction condition: 2.0 mmol MeL, 100 mg catalyst (M=0.05 mmol, 0.025 mmol Re), 8 g MeOH, 50 bar $H_2$ gas pressure, 12 hours reaction time, 220° C. reaction temperature, 40 mg naphthalene (internal standard). Catalyst activated at 450° C. in air followed by reduction at 300° C. for 3 hours under formier gas flow (10 vol. % $H_2$ in $N_2$, 50 ml/min).

TABLE 2

MeL to MeP conversion with M-Re/$ZrO_2$ catalysts (M = Ru, Rh, Ag, Au, Ir, Pd and Pt)[a]

| Entry | Catalyst | % MeL conv. | % MeP Yield |
|---|---|---|---|
| 1 | Ru—Re/$ZrO_2$ | 86 | 30 |
| 2 | Rh—Re/$ZrO_2$ | 55 | 25 |
| 3 | Ag—Re/$ZrO_2$ | 94 | 40 |
| 4 | Au—Re/$ZrO_2$ | 97 | 54 |
| 5 | Ir—Re/$ZrO_2$ | 92 | 46 |
| 6 | Pd—Re/$ZrO_2$ | 77 | 29 |
| 7 | Pt—Re/$ZrO_2$ | 73 | 23 |
| 8 | Fe—Re/$ZrO_2$ | >99 | 60 |

The catalysts and support material were synthesised using techniques known to the skilled person in the art. The bimetallic catalysts were made of 0.05 mmol M and 0.025 mmol Re or 4.71 wt % Re (for 100 mg catalyst). The catalysts were activated at 450° C. in air followed by reduction at 300° C. for 3 hours under formier gas flow (10 vol. % $H_2$ in $N_2$, 50 ml/min).

The catalytic reaction was carried out in a batch process with 2.0 mmol MeL (208.12 mg), 100 mg catalyst, 8 g methanol (MeOH), 40 mg naphthalene, and at 50 bar $H_2$ gas pressure, and with 12 hours reaction time, and at 220° C. reaction temperature.

From Table 2 it is seen that the catalysts bearing the precious metal catalyst Ag, Au and Ir showed >90% MeL conversion with better MeP yields (40-55%) compared to for Ru, Rh, Pd and Pt containing M-Re/$ZrO_2$ catalyst (MeP yield=20-30%).

It was also seen that the Fe—Re/$ZrO_2$ catalyst (cf. Table 2, entry 8) comprising non-precious and cheaper raw material Fe, showed better activity compared to Ru—Re/$ZrO_2$ catalyst and >99% MeL conversion as well as 60% yield of MeP was achieved. The result demonstrated that it is possible to obtain high catalytic performance in MeL hydrogenolysis based on partially replaced non-precious metals.

Example 3

$ZrO_2$ Supported Non-precious Catalysts

The catalytic performance in the methyl lactate (MeL) hydrogenolysis process was tested for $ZrO_2$ supported catalysts comprising no precious metals. Catalyst comprising iron, of the type Fe-M/$ZrO_2$, where M was Mo, Mn, Ni, Co, Cu, Zn, were tested, as well as the $ZrO_2$ supported monometallic catalysts Fe/$ZrO_2$ and Ni/$ZrO_2$.

The results are summarised in Table 3, showing the MeL conversion (Conv.) in %, and the MeP yield in %. [a] Reaction condition: 2.0 mmol MeL, 100 mg catalyst (Fe=0.05 mmol or 2.68 wt %, M=0.025 mmol), 8 g MeOH, 50 bar $H_2$ gas pressure, 12 hours reaction time, 220° C. reaction temperature, 40 mg naphthalene (internal standard), [b] non-reduced catalyst, [c] Ni=0.05 mmol. Catalyst activated at 450° C. in air followed by reduction at 300° C. for 3 hours under formier gas flow (10 vol. % $H_2$ in $N_2$, 50 ml/min).

TABLE 3

MeL to MeP conversion with Fe-M/$ZrO_2$ catalyst (M = Mn, Mo, Ni, Co, Cu and Zn)[a]

| Entry | Catalyst | % MeL Conv. | % MeP yield |
|---|---|---|---|
| 1 | Fe/$ZrO_2$ | 85 | 45 |
| 2 | Fe—Mo/$ZrO_2$ | >99 | 47 |
| 3 | Fe—Mn/$ZrO_2$ | 88 | 33 |
| 4 | Fe—Ni/$ZrO_2$ | >99 | 73 |
| 5 | Fe—Co/$ZrO_2$ | >99 | 71 |
| 6 | Fe—Cu/$ZrO_2$ | >99 | 36 |
| 7 | Fe—Zn/$ZrO_2$ | 74 | 40 |
| 8 | Fe—Ni/$ZrO_2$[b] | 87 | 64 |
| 9 | Ni/$ZrO_2$[c] | 34 | 4 |

The catalysts and support material were synthesised using techniques known to the skilled person in the art. The bimetallic catalysts were made of 0.05 mmol or 2.68 wt % Fe and 0.025 mmol M (for 100 mg catalyst). The Ni/$ZrO_2$ catalyst was made of 0.05 mmol or 2.79 wt % Ni (for 100 mg catalyst). The catalysts were activated at 450° C. in air followed by reduction at 300° C. for 3 hours under formier gas flow (10 vol. % $H_2$ in $N_2$, 50 ml/min). In one case, the Fe—Ni/$ZrO_2$ catalyst was not reduced (entry 8 in Table 3).

The catalytic reaction was carried out in a batch process with 2.0 mmol MeL (208.12 mg), 100 mg catalyst, 8 g methanol (MeOH), 40 mg naphthalene, and at 50 bar $H_2$ gas pressure, and with 12 hours reaction time, and at 220° C. reaction temperature.

From Table 3, entry 1, it is seen that the supported monometallic Fe/ZrO$_2$ catalyst showed 85% MeL conversion with 45% MeP yield. Doping the Fe catalyst with a further non-precious metal was seen to have different effect. Fe—Mo/ZrO$_2$ showed 47% MeP yield which was similar to the Fe/ZrO$_2$ catalysts. The Mn, Cu and Zn metals doping displayed inhibiting effect on the activity of Fe/ZrO$_2$ catalyst (cf. Table 3, entry 3, 6 and 7). Lower activity was observed for the monometallic Ni/ZrO$_2$.

On the other hand the Ni and Co metals were seen to enhance the activity of the catalyst and >99% MeL conversion as well as >70% MeP yield was achieved (cf. entry 4 and 5 in Table 3). Thus, it was demonstrated that surprisingly high catalytic performance in MeL hydrogenolysis based on non-precious metals could be obtained.

The non-reduced Fe—Ni/ZrO$_2$ catalyst showed a comparable yield in the reaction (64% MeP) compared to the corresponding reduced catalyst with 73% yield (cf. Table 3, entries 4 and 8). This surprising result is further described in Example 7.

Example 4

Different Supported Fe—Ni Catalyst

The supported non-precious and bimetallic Fe—Ni catalysts (0.05 mmol or 2.68 wt % Fe and 0.025 mmol or 1.40 wt % Ni for 100 mg catalyst) were tested on different types of support material, i.e. TiO$_2$, γ-Al$_2$O$_3$, SiO$_2$, MgAl$_2$O$_4$ (spinel) and AC (activated carbon) for the hydrogenolysis reaction of MeL. The same fabrication procedure and test conditions as described in Example 3 were applied.

The results are summarised in Table 4. For the comparison, Fe—Ni/ZrO$_2$ was also included in Table 4. [a] Reaction condition: 2.0 mmol MeL, 100 mg catalyst (Fe=0.05 mmol or 2.68 wt %, Ni=0.025 mmol or 1.40 wt %), 8 g MeOH, H$_2$ pressure 50 bar, 12 hours reaction time, 220° C. reaction temperature, 40 mg naphthalene (internal standard). Catalyst activated at 450° C. in air followed by reduction at 300° C. for 3 hours under formier gas flow (10 vol. % H$_2$ in N$_2$, 50 ml/min, [b] Catalyst activated at 450° C. under Ar flow (50 ml/min).

TABLE 4

MeL to MeP conversion with Fe—Ni/Support
(Support = ZrO$_2$, TiO$_2$, Al$_2$O$_3$, SiO$_2$, MgAl$_2$O$_4$, AC)[a]

| Entry | Catalyst | % MeL conv. | % MeP yield |
|---|---|---|---|
| 1 | Fe—Ni/ZrO$_2$ | >99 | 73 |
| 2 | Fe—Ni/TiO$_2$ | 64 | 47 |
| 3 | Fe—Ni/Al$_2$O$_3$ | 44 | 11 |
| 4 | Fe—Ni/SiO$_2$ | 35 | 24 |
| 5 | Fe—Ni/MgAl$_2$O$_4$ | 29 | 8 |
| 6 | Fe—Ni/AC[b] | 20 | 3 |

The MeP yield on the supported Fe—Ni catalysts were decreased in the order of ZrO$_2$>>TiO$_2$>SiO$_2$>γ-Al$_2$O$_3$>MgAl$_2$O$_4$>AC. Thus, the best catalytic response of the Fe—Ni bimetallic catalyst was obtained with the ZrO$_2$ support.

Example 5

Fe—Ni/ZrO$_2$ Catalysts with Different Fe/Ni Molar Ratios

Fe—Ni/ZrO$_2$ catalysts with different Fe/Ni molar ratios, by changing the amount of Ni while keeping the amount of Fe constant, were synthesized, and tested for hydrogenolysis of the MeL to MeP, as described in Example 3. The results are summarised in FIG. 1.

Figure 1:
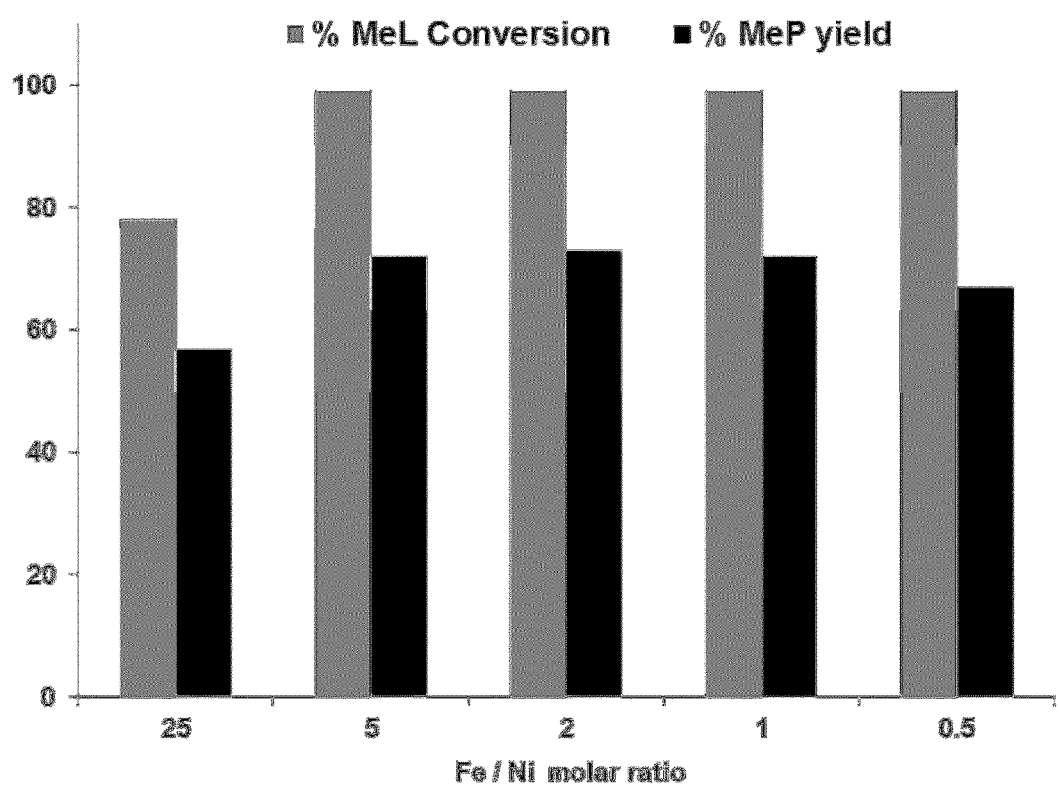
FIG. 1 shows the results of Example 5, and illustrates the catalytic activity in the methyl lactate (MeL) hydrogenolysis process as the conversion of MeL and the yield of MeP, for Fe—Ni/$ZrO_2$ catalysts with different Fe/Ni molar ratios. Reaction conditions: 2.0 mmol MeL, 100 mg catalyst (Fe=0.05 mmol or 2.68 wt %), 220° C. reaction temperature, 8 g MeOH, 50 bar $H_2$ gas pressure, 12 hours reaction time, 40 mg naphthalene (internal standard). Catalyst activated at 450° C. in air followed by reduction at 300° C. for 3 hours under formier gas flow (10 vol. % $H_2$ in $N_2$, 50 ml/min).

From FIG. 1 it was seen that the Ni metal has a promoting effect in the hydrogenolysis of MeL even at Fe/Ni molar ratio=25. At this concentration the yield of MeP is increased to 57%, as compared to the Fe/ZrO$_2$ catalyst with 45% MeP yield (cf. Table 3, entry 1).

As the Ni concentration increases with Fe/Ni molar ratio from 25 to 5, the Fe—Ni/ZrO$_2$ catalyst showed >99% MeL conversion with 73% MeP yield. Further increase in the Ni concentration did not increase the MeP yield significantly, and identical performance was observed with Fe/Ni molar ratios 5, 2, and 1. For the ratio 0.5, a minor decrease in the yield was observed due to decrease in the selectivity (67% selectivity to MeP).

Example 6

Reaction Temperature and Time

Fe—Ni/ZrO$_2$ catalysts were made as described in Example 3, and the influence of the reaction temperature and time on the MeL hydrogenolysis process was tested. The catalytic reaction was carried out in a batch process with 2.0 mmol MeL (208.12 mg), 100 mg catalyst (0.05 mmol or 2.68 wt % Fe and 0.025 mmol or 1.40 wt % Ni), 8 g methanol (MeOH), 40 mg naphthalene, and at 50 bar H$_2$ gas pressure. The catalysts were activated at 450° C. in air followed by reduction at 300° C. for 3 hours under formier gas flow (10 vol. % H$_2$ in N$_2$, 50 ml/min). The results are shown in FIGS. 2 and 3.

Figure 2:
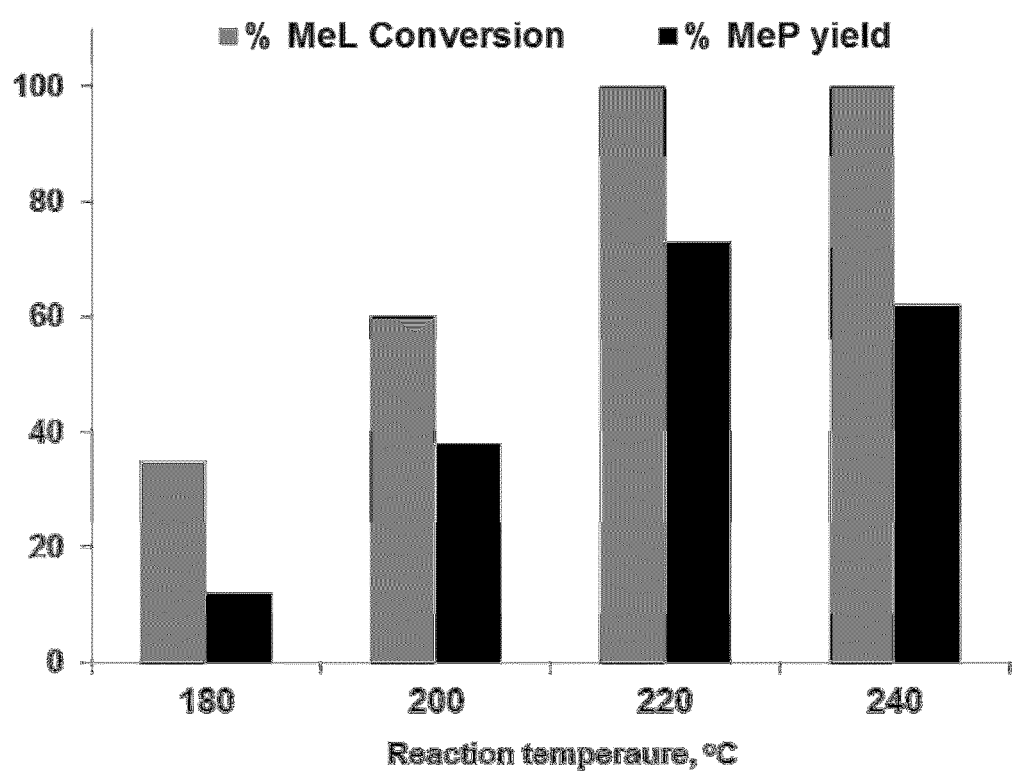
FIG. 2 shows the results of Example 6, and illustrates the catalytic activity in the methyl lactate (MeL) hydrogenolysis process as the conversion of MeL and the yield of MeP, for Fe—Ni/$ZrO_2$ catalysts at different reaction temperatures. Reaction conditions: 2.0 mmol MeL, 100 mg catalyst (Fe=0.05 mmol or 2.68 wt. %, Ni=0.025 mmol or 1.40 wt %), 8 g MeOH, 50 bar $H_2$ gas pressure, 12 hours reaction time, 40 mg naphthalene (internal standard). Catalyst activated at 450° C. in air followed by reduction at 300° C. for 3 hours under formier gas flow (10 vol. % $H_2$ in $N_2$, 50 ml/min).

FIG. 2 shows that the MeL conversion and the yield for MeP increased linearly with increased reaction temperature from 180 to 220° C. At 220° C. the reaction showed >99% MeL conversion and a 73% MeP yield. However, upon further increase in the reaction temperature to 240° C., the MeP yield decreased to 60%.

Figure 3:
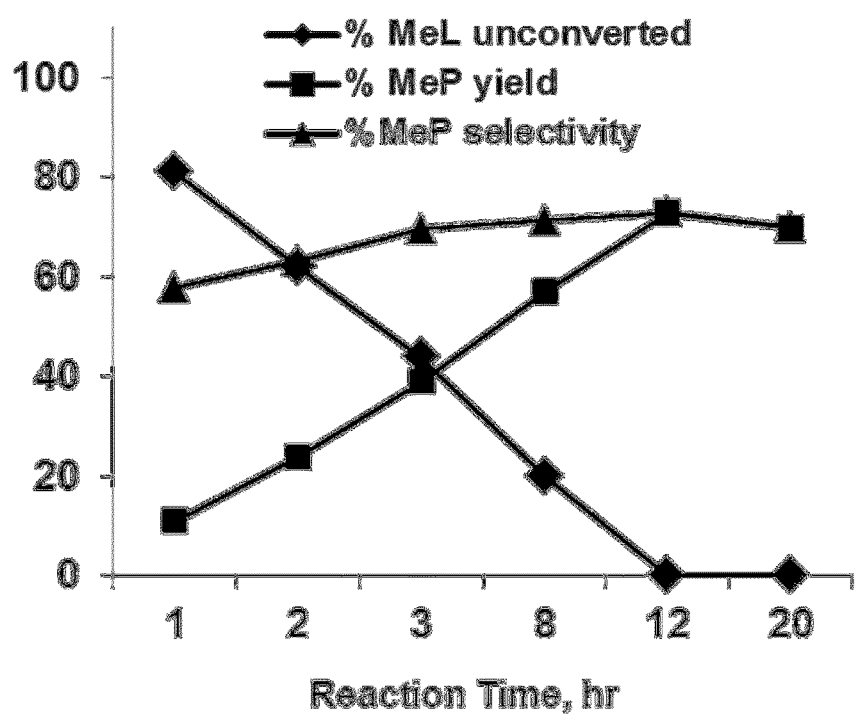
FIG. 3 shows the results of Example 6, and illustrates the catalytic activity in the methyl lactate (MeL) hydrogenolysis process as the unconverted MeL, the yield of MeP, and the selectivity of MeP, for Fe—Ni/$ZrO_2$ catalysts at different reaction times. Reaction conditions: 2.0 mmol MeL, 100 mg catalyst (Fe=0.05 mmol or 2.68 wt %, Ni=0.025 mmol or 1.40 wt %), 8 g MeOH, 50 bar $H_2$ gas pressure, 220° C. reaction temperature, 40 mg naphthalene (internal standard). Catalyst activated at 450° C. in air followed by reduction at 300° C. for 3 hours under formier gas flow (10 vol. % $H_2$ in $N_2$, 50 ml/min).

FIG. 3 shows that the reaction time influenced on the catalytic performance. The reactions were performed at different reaction times, i.e. 1, 2, 3, 8, 12 and 20 hours. It was observed that both reaction conversion and MeP selectivity increased with time. At 12 hours of reaction time >99% conversion of the MeL was observed with 73% MeP selectivity. Further increasing the reaction time to 20 hours was seen to result in a minor decrease in MeP yield to 60%.

Example 7

Hydrogen Source

Fe—Ni/ZrO$_2$ catalysts were made as described in Example 3, and the influence of the partial pressure of H$_2$ gas on the activity of the Fe—Ni/ZrO$_2$ catalyst in the MeL hydrogenolysis process was tested. The catalytic reaction was carried out in a batch process with 2.0 mmol MeL (208.12 mg), 100 mg catalyst (0.05 mmol or 2.68 wt % Fe and 0.025 mmol or 1.40 wt % Ni), 8 g methanol (MeOH), 40 mg naphthalene, with 12 hours reaction time, and at 220° C. reaction temperature, and at a total 50 bar gas pressure. For the tests with varying amounts of H$_2$ gas, N$_2$ was used as makeup gas to obtain the 50 bar at the reaction. The catalysts were activated at 450° C. in air followed by reduction at 300° C. for 3 hours under formier gas flow (10 vol. % H$_2$ in N$_2$, 50 ml/min). The results are shown in FIG. 4.

A hydrogen source is needed for the hydrogenolysis reaction. The hydrogen may be introduced directly as molecular $H_2$ gas. FIG. 4 shows that increasing the partial pressure of the hydrogen gas from 5 vol. % $H_2$, to 10 vol. % $H_2$, resulted in a minor increase in the yield and selectivity. With 5 vol % or 10 vol % of $H_2$, yields of respectively 67 and 71% MeP was obtained. Further increasing the hydrogen content to pure $H_2$ gas did not effectively increase the yield of MeP (73%).

Thus, using the Fe—Ni/$ZrO_2$ catalysts of the invention, expensive pure $H_2$ gas can be avoided and replaced by the cheaper at more safely handled formier gas mixture (10 vol % $H_2$ in $N_2$).

FIG. 4 further surprisingly showed the possibility of relatively high catalytic activity of the Fe—Ni catalyst in the absence of directly added molecular $H_2$. Two types of Fe—Ni catalysts were tested in pure $N_2$ gas, reduced and non-reduced Fe—Ni catalysts, as described in Example 3. The non-reduced catalyst is indicated as N2(a) in FIG. 4, and showed 35% MeP yield, whereas the reduced catalyst showed 62% MeP yield in pure $N_2$. The non-reduced Fe—Ni catalyst was blackish after the reaction, indicating the formation of reduced metallic species.

The observed catalytic activity in the pure $N_2$ atmosphere can be ascribed to in-situ generation of molecular $H_2$ due to catalytic decomposition of the organic solvent, in this case methanol ($CH_3OH$). The molecular $H_2$, which originated from MeOH, will both assist in the hydrogenolysis process, as well as assist in the reduction of any non-reduced Fe and Ni oxide species, such as in the case with non-reduced catalyst.

Example 8

MeL Concentration

Fe—Ni/$ZrO_2$ catalysts were made as described in Example 3, and the influence of the influence of the MeL concentration on the activity of the Fe—Ni/$ZrO_2$ catalyst in the MeL hydrogenolysis process was tested.

The results are summarised in Table 5, which shows the catalytic activity in the methyl lactate (MeL) hydrogenolysis process (as the conversion of MeL, yield of MeP, and MeP selectivity) of Fe—Ni/$ZrO_2$ catalysts at different MeL concentrations. The reaction conditions: [a]Reaction condition: 100 mg catalyst (Fe=0.05 mmol or 2.68 wt. %, Ni=0.025 mmol or 1.40 wt. %, 8 gm MeOH, 12 hours reaction time, 220° C. reaction temperature, 50 bar $H_2$ gas pressure, 40 mg naphthalene (internal standard). Catalyst activated at 450° C. in air followed by reduction at 300° C. for 3 hours under formier gas flow (10 vol. % $H_2$ in $N_2$, 50 ml/min), [b]24 hours of reaction time.

TABLE 5

MeL to MeP conversion with Fe—Ni/$ZrO_2$ with different MeL concentrations.[a]

| Entry | MeL conc. | % MeL conv. | % MeP Yield | % MeP select. |
|---|---|---|---|---|
| 1 | 2 mmol | >99 | 73 | 73 |
| 2 | 5 mmol | 52 | 41 | 78 |
| 3 | 7.5 mmol | 42 | 30 | 71 |
| 4 | 5 mmol[b] | 94 | 75 | 80 |

The results shown in the previous Examples 4 and 6 are included in Table 5 (entry 1), and it was seen that Fe—Ni/$ZrO_2$ was able to convert more than 99% of MeL in the period of 12 hours. The result was obtained with a MeL concentration of 2 mmol.

The concentration of MeL was increased from 2 mmol to 5 or 7.5 mmol in the reaction mixture, and the reaction was performed for similar period. The MeL conversion and MeP yield decreased gradually with the increase in MeL concentration in the reaction mixture.

Despite the decrease in yield, it was observed that high selectivity (>70% MeP selectivity) was achieved at the various MeL concentrations used in the reaction mixture. This indicated that any excess amount of MeL remains stable in the reaction mixture even at high temperature and pressure rather than following undesirable reaction pathways. This was further supported by the catalytic experiment with 5 mmol MeL concentration for 24 hours (denoted with (b) in Table 5). In this reaction period, the conversion and yield was increased significantly with 80% MeP selectivity (cf. Table 5, entry 2 and 4).

Example 9

Catalyst Recycling

The recyclability and stability of the Fe—Ni/$ZrO_2$ catalyst was evaluated by MeL hydrogenolysis reaction with 5 consecutive catalytic runs for 3 hours each. The results are shown in FIG. 5.

The Fe—Ni/$ZrO_2$ catalysts with Fe/Ni molar ratio 5, were fabricated as described in Examples 3-4, and the tests were carried out in batch processes with 4 mmol MeL (416.24 mg), 200 mg catalyst (Fe=0.1 mmol or 2.68 wt % and Ni=0.02 mmol or 0.58 wt %), 16 g MeOH, 3 hours reaction time, 220° C. reaction temperature, 50 bar $H_2$ gas pressure, naphthalene (internal standard). The catalyst was activated at 450° C. in air followed by reduction at 300° C. for 3 hours under formier gas flow (10 vol. % $H_2$ in $N_2$, 50 ml/min).

The catalyst recyclability was tested at low reaction conversion (<30%), thus each consecutive catalytic reaction was carried out for 3 hours.

In order to maintain the MeL/(Fe+Ni) molar ratio constant at 33.33, the MeL addition in each consecutive catalytic reaction was decreased corresponding to the decrease in the catalyst quantity observed after each catalytic run.

The Fe—Ni/$ZrO_2$ catalyst was found to be efficiently recyclable for MeL hydrogenolysis and ≈25% MeL conversion and ≈20% MeP yield was achieved after each catalytic run. The constant activity and selectivity of the catalyst indicated that the catalytic system was active, recyclable and stable under the used reaction conditions.

Example 10

Substrates

The Fe—Ni/$ZrO_2$ catalyst was tested for the hydrogenolysis of other substrates than methyl lactate (MeL). The hydrogenolysis of other bio-derived alpha-hydroxy esters, i.e. ethyl lactate, 2-propyl lactate and 1-butyl lactate was tested.

The results are shown in Table 6, showing the catalytic activity in the alkyl lactate hydrogenolysis process as the conversion of alkyl lactates and yield of alkyl propionate, for Fe—Ni/$ZrO_2$ catalysts using different alpha-hydroxy ester substrates.

TABLE 6

Hydrogenolysis of α-hydroxy esters (ethyl lactate,
2-propyl lactate and 1-butyl lactate) with Fe—Ni/ZrO$_2$

| Entry | α-hydroxy esters | % Alkyl Lactates Conv. | % Alkyl propionate Yield |
|---|---|---|---|
| 1 | Methyl lactate | >99 | 72 |
| 2 | Ethyl lactate | >99 | 68 |
| 3 | 2-propyl lactate | >99 | 71 |
| 4 | 1-butyl lactate | >99 | 67 |

The Fe—Ni/ZrO$_2$ catalysts were fabricated as described in Example 3, and the tests were carried out in a batch process with 2.0 mmol of other a-hydroxy esters such as ethyl lactate, 2-propyl lactate and 1-butyl lactate, 100 mg catalyst (Fe=0.05 mmol or 2.68 wt % and Ni=0.01 mmol or 0.58 wt %), 8 g of solvent (i.e. methanol (MeOH) or ethanol (EtOH) or iso-propanol, or 1-butanol), 12 hours reaction time, 220° C. reaction temperature, 50 bar H$_2$ gas pressure, and naphthalene (internal standard). The catalyst was activated at 450° C. in air followed by reduction at 300° C. for 3 hours under formier gas flow (10 vol. % H$_2$ in N$_2$, 50 ml/min).

As seen in Table 6, the catalytic system was found to be active and selective with more than 99% alkyl lactate conversions, as well as >65% selectivities for all the substrates and corresponding alkyl propionates.

Example 11

Metal Ferrite Catalysts

The catalytic performance in the methyl lactate (MeL) hydrogenolysis process was tested for metal ferrite catalysts such as nickel ferrite (NiFe$_2$O$_4$), and cobalt ferrite (CoFe$_2$O$_4$).

The results are summarised in Table 7, showing the MeL conversion (Conv.) in %, and the MeP yield in %. The reaction conditions were: 2.0 mmol MeL, 100 mg catalyst, 8 g MeOH, 50 bar H$_2$ gas pressure, 12 hours reaction time, 220° C. reaction temperature, 40 mg naphthalene (internal standard). Catalyst reduced at 300° C. for 3 hours under formier gas flow (10 vol. % H$_2$ in N$_2$, 50 ml/min).

TABLE 7

MeL to MeP conversion with metal ferrite catalyst under the reaction
conditions: 2.0 mmol MeL, 100 mg catalyst, 8 g MeOH, 50 bar H$_2$ gas
pressure, 12 hours reaction time, 220° C. reaction temperature,
40 mg naphthalene (internal standard). Catalyst reduced at 300° C.
for 3 hours under formier gas flow (10 vol. % H$_2$ in N$_2$, 50 ml/min).

| Entry | Catalyst | % MeL conv. | % MeP Yield |
|---|---|---|---|
| 1 | Nickel ferrite | >99 | 75 |
| 2 | Cobalt ferrite | >99 | 71 |

Items

The invention can be further described by the items listed below.

Item 1

A method for hydrogenolysis of alpha-hydroxy esters or acids, comprising:
reacting the alpha-hydroxy ester or acid in the presence of a solid catalyst and a catalyst support,
wherein the catalyst comprises at least one metal selected from the group of metals belonging to groups 6-12 and periods 4-6 of the periodic table, and
wherein the catalyst support is a porous solid material with the proviso that the porous solid material is not consisting of SiO$_2$.

Item 2

The method according to item 1, wherein the catalyst comprises at least one metal selected from the group of: Cr, Mn, Fe, Co, Ni, Cu, Zn, Mo, Ru, Rh, Pd, Ag, Cd, W, Re, Os, Ir, Pt, Au, Hg, and combinations thereof, more preferably selected from the group of: Mn, Fe, Co, Ni, Cu, Zn, Re, Pt, Au, and combinations thereof, and most preferably selected from the group of: Mn, Fe, Co, Ni, Cu, Zn, and combinations thereof.

Item 3

The method according to any of the preceding items, wherein the catalyst is a bimetallic compound comprising iron (Fe), more preferably selected from the group of: Fe—Re, Fe—Mo, Fe—Mn, Fe—Cu, Fe—Co, and Fe—Ni, most preferably selected from the group of: Fe—Co, and Fe—Ni.

Item 4

The method according to any of items 1-2, wherein the catalyst is a bimetallic compound comprising rhenium (Re), more preferably selected from the group of: Ru—Re, Rh—Re, Ag—Re, Au—Re, Ir—Re, Pd—Re, Pt—Re, Fe—Re, most preferably selected from the group of: Ru—Re, Ag—Re, Au—Re and Fe—Re.

Item 5

The method according to any of the preceding items, wherein the catalyst support comprises one or more metal oxide(s), and/or a thermally stable polymer, and/or activated carbon, with the proviso that if the support consists of one metal oxide, said metal oxide is not SiO$_2$.

Item 6

The method according to item 5, wherein the catalyst support is a metal oxide, with the proviso that said metal oxide is not SiO$_2$.

Item 7

The method according to any of items 5-6, wherein the metal oxide is selected from the group of: ZrO$_2$, TiO$_2$, Al$_2$O$_3$, MgAl$_2$O$_4$, zeolites, combinations thereof, and any combination with SiO$_2$, more preferably selected from the group of: ZrO$_2$ and TiO$_2$, and most preferably is ZrO$_2$.

Item 8

The method according to item 5, wherein the catalyst support is a thermally stable polymer selected from the group of: polyether (ether) ketone (PEEK), polyethersulfone (PES), polyphenylquinoxaline (PPQ), polybenzimidazole (PBI), polyimide (PI), poly(arylene ether), poly(imino ether), polyaniline, polyphenylene, polydivinylbenzene (PDVB), polyacrylates (PA), and poly-methylmethacrylates (PMMA).

Item 9

The method according to any of the preceding items, wherein the catalyst support is microporous and/or mesoporous.

Item 10

The method according to any of the preceding items, wherein the alpha-hydroxy ester has the formula:

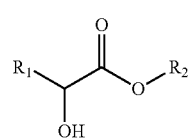

wherein $R_1$ and $R_2$ are independently selected from the group of: hydrogen, alkyl, halogenated alkyl, aminoalkyl, hydroxyalkyl, alkoxyalkyl, alkenyl, alkynyl, aryl, heteroaryl, cycloalkyl, cycloalkenyl, heterocycloalkyl, and heterocycloalkenyl.

Item 11
The method according to item 10, wherein the alpha-hydroxy ester is an alkyl lactate.

Item 12
The method according to item 11, wherein the alkyl lactate is methyl lactate.

Item 13
The method according to any of items 10-12, wherein $R_1$ and $R_2$ are independently selected from $C_1$-$C_9$ alkyl and hydrogen, more preferably $C_1$-$C_3$ alkyl and hydrogen, and most preferably $R_1$ is methyl and $R_2$ is methyl or hydrogen.

Item 14
The method according to any of the preceding items, wherein the process is carried out at elevated pressure and temperature, and in the presence of a hydrogen source.

Item 15
The method according to item 14, wherein the hydrogen source is a gas comprising $H_2$ and/or a component decomposing into hydrogen, more preferably the hydrogen sourse is a gas comprising $H_2$.

Item 16
The method according to any of items 14-15, wherein the hydrogen source is selected from the group of: alcohols, methyl formate, formic acid, diimide, and hydrazine, more preferably selected from the group of: methanol, ethanol, butanol, propanol and isopropanol, and most preferably is methanol.

Item 17
A method for producing propionic acid ester with the formula:

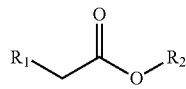

wherein $R_1$ is methyl, and $R_2$ is selected from the group of: hydrogen, alkyl, halogenated alkyl, aminoalkyl, hydroxyalkyl, alkoxyalkyl, alkenyl, alkynyl, aryl, heteroaryl, cycloalkyl, cycloalkenyl, heterocycloalkyl, and heterocycloalkenyl, comprising the steps of:
(i) providing an alpha-hydroxy ester or acid,
(ii) providing a solid catalyst and a catalyst support, wherein the catalyst comprises at least one metal selected from the group of metals belonging to groups 6-12 and periods 4-6 of the period table, and wherein the catalyst support is a solid material with the proviso that the solid material cannot consist of $SiO_2$, and
(iii) reacting the alpha-hydroxy ester in the presence of the catalyst and catalyst support,
where by the alpha-hydroxy ester is converted into propionic acid ester.

Item 18
The method according to item 17, wherein the propionic acid ester is selected from the group of: alkyl propionate, aryl propionate, and alkenyl propionate.

Item 19
The method according to items 17-18, wherein the propionic acid ester is alkyl propionate.

Item 20
The method according to items 17-18, wherein the propionic acid ester is methyl propionate.

Item 21
The method according to item 17, wherein the alpha-hydroxy ester is an alkyl lactate.

Item 22
The method according to item 21, wherein the alkyl lactate is methyl lactate.

Item 22
The method according to item 17, wherein step (iii) is carried out at elevated pressure and temperature, and in the presence of a hydrogen source.

Item 23
The method according to item 22, wherein the hydrogen source is a gas comprising $H_2$ and/or a component decomposing into hydrogen, more preferably the hydrogen sourse is a gas comprising $H_2$.

Item 24
The method according to any of items 22-23, wherein the hydrogen source is selected from the group of: alcohols, methyl formate, formic acid, diimide, and hydrazine, more preferably selected from the group of: methanol, ethanol, butanol, propanol and isopropanol, and most preferably is methanol.

Item 25
The method according to any of items 1-25, wherein the method is selected from the group of: a batch process, a continuous process, such as a continuous flow fixed-bed process and/or fluidized-bed flow process.

Item 25
Use of the methods according to any of items 1-24 for the production of propionic acid esters, such as alkyl propionate, more preferably methyl propionate, ethyl propionate, and butyl propionate.

The invention claimed is:
1. A method for hydrogenolysis of alpha-hydroxy esters or acids, comprising:
reacting the alpha-hydroxy ester or acid in the presence of a solid catalyst and a catalyst support,
wherein the catalyst comprises at least two different metals that are Cr, Mn, Fe, Co, Ni, Cu, Zn, Mo, Ru, Rh, Pd, Ag, Cd, W, Re, Os, Ir, Pt, Au, or Hg, or a combination thereof, and
wherein the catalyst support is a porous solid material with the proviso that if the porous solid material consists of one metal oxide, the metal oxide is not $SiO_2$.
2. The method according to claim 1, wherein the catalyst is a bimetallic compound comprising iron (Fe), or wherein the catalyst is a bimetallic compound comprising rhenium (Re).
3. The method according to claim 1, wherein the catalyst support comprises one or more metal oxide(s), and/or a thermally stable polymer, and/or activated carbon, and/or wherein the catalyst support is microporous and/or mesoporous.
4. The method according to claims 3, wherein the metal oxide is selected from the group consisting of: $ZrO_2$, $TiO_2$, $Al_2O_3$, $MgAl_2O_4$, zeolites, combinations thereof, and any combination with $SiO_2$.
5. The method according to claim 1, wherein the alpha-hydroxy ester or acid has the formula:

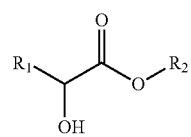

wherein $R_1$ and $R_2$ are independently selected from the group consisting of: hydrogen, alkyl, halogenated alkyl, aminoalkyl, hydroxyalkyl, alkoxyalkyl, alkenyl, alkynyl, aryl, heteroaryl, cycloalkyl, cycloalkenyl, heterocycloalkyl, and heterocycloalkenyl.

6. The method according to claim 5, wherein the alpha-hydroxy ester is an alkyl lactate.

7. The method according to claim 6, wherein the alkyl lactate is methyl lactate.

8. The method according to claim 5, wherein $R_1$ and $R_2$ are independently $C_1$-$C_9$ alkyl or hydrogen.

9. The method according to claim 1, wherein the process is carried out at elevated pressure and temperature, and in the presence of a hydrogen source.

10. The method according to claim 9, wherein the hydrogen source is a gas comprising $H_2$ and/or a component decomposing into hydrogen.

11. A method for producing propionic acid ester or acid with the formula:

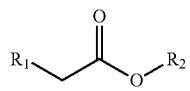

wherein $R_1$ is methyl, and
$R_2$ is selected from the group consisting of hydrogen, alkyl, halogenated alkyl, aminoalkyl, hydroxyalkyl, alkoxyalkyl, alkenyl, alkynyl, aryl, heteroaryl, cycloalkyl, cycloalkenyl, heterocycloalkyl, and heterocycloalkenyl, comprising the steps of:
(i) providing an alpha-hydroxy ester or acid,
(ii) providing a solid catalyst and a catalyst support, wherein the catalyst comprises at least two different metals that are Cr, Mn, Fe, Co, Ni, Cu, Zn, Mo, Ru, Rh, Pd, Ag, Cd, W, Re, Os, Ir, Pt, Au, or Hg, or a combination thereof, and
wherein the catalyst support is a solid material with the proviso that if the porous solid material consists of one metal oxide, the metal oxide is not $SiO_2$, and
(iii) reacting the alpha-hydroxy ester or acid in the presence of the catalyst and catalyst support,
whereby the alpha-hydroxy ester or acid is converted into propionic acid ester or propionic acid.

12. The method according to claim 11, wherein the alpha-hydroxy ester is an alkyl lactate, and/or wherein the propionic acid ester is selected from the group consisting of: alkyl propionate, aryl propionate, and alkenyl propionate.

13. The method according to claim 12, wherein the alkyl lactate is methyl lactate, and/or wherein the propionic acid ester is methyl propionate.

14. The method according to claim 11, wherein step (iii) is carried out at elevated pressure and temperature, and in the presence of a hydrogen source.

15. The method according to claim 14, wherein the hydrogen source is a gas comprising $H_2$ and/or a component decomposing into hydrogen.

16. The method according to claim 1, wherein the method is selected from the group consisting of: a batch process, a continuous process, such as a continuous flow fixed-bed process and/or fluidized-bed flow process.

17. The method according to claim 11, wherein the method is selected from the group consisting of: a batch process, a continuous process, such as a continuous flow fixed-bed process and/or fluidized-bed flow process.

18. The method according to claim 1, wherein the catalyst is a ferrite.

19. The method according to claim 18, wherein the catalyst is nickel ferrite ($NiFe_2O_4$) and/or cobalt ferrite ($CoFe_2O_4$).

* * * * *